US010821083B2

(12) United States Patent
Zapotoczny et al.

(10) Patent No.: US 10,821,083 B2
(45) Date of Patent: Nov. 3, 2020

(54) NANOCAPSULE FOR DELIVERY OF LIPOPHILIC COMPOUND AND PROCESS OF PREPARATION THEREOF

(71) Applicant: CHDE POLSKA SA, Rzeszow (PL)

(72) Inventors: Szczepan Zapotoczny, Cracow (PL); Joanna Szafraniec, Cracow (PL)

(73) Assignee: CHDE POLSKA SA, Rzeszow (PL)

( * ) Notice: Subject to any disclaimer, the term of this patent is extended or adjusted under 35 U.S.C. 154(b) by 0 days.

(21) Appl. No.: 15/743,728

(22) PCT Filed: Jul. 12, 2016

(86) PCT No.: PCT/PL2016/050032
§ 371 (c)(1),
(2) Date: Jan. 11, 2018

(87) PCT Pub. No.: WO2017/014655
PCT Pub. Date: Jan. 26, 2017

(65) Prior Publication Data
US 2018/0200197 A1    Jul. 19, 2018

(30) Foreign Application Priority Data
Jul. 17, 2015 (PL) .......................... 413155

(51) Int. Cl.
*A61K 9/00* (2006.01)
*A61K 9/51* (2006.01)
*A61K 9/10* (2006.01)

(52) U.S. Cl.
CPC ............. *A61K 9/5161* (2013.01); *A61K 9/10* (2013.01); *A61K 9/5123* (2013.01); *A61K 9/5176* (2013.01)

(58) Field of Classification Search
CPC ................................................... A61K 9/5161
See application file for complete search history.

(56) References Cited

PUBLICATIONS

Szafranciec, Robust oil-core nanocapsules with hyaluronate-based shells as promising nanovehciles for lipophilic compounds, Nanoscale, 2017, 9, 18867-18880.*
Nichifor Marieta et al: Micelle-like association of polysaccharides with hydrophobic end groups, Carbohydrate Polymers. vol. 110. 3 Apr. 1, 2014 (Apr. 3, 2014). pp. 209-218.
Hongqiang Wang et al: Sono-Assembly of Highly Biocompatible Polysaccharide Capsules for Hydrophobic Drug Delivery . Advanced Healthcare Materials. vol. 3. No. 6. Jun. 1, 2014 (Jun. 1, 2014). pp. 825-831.
Hassan Namazi et al: Nanoparticles Based on Modified Polysaccharides In: The Delivery of Nanoparticles—May 16, 2012 (May 16, 2012).
Lin L H et al: Surface activity and emulsification properties of hydrophobically modified dextrins• Colloids and Surfaces. A. Physicachemical and Engineering Aspects. Elsevier. Amsterdam. NL. vol. 364. No. 1-3. Jul. 20, 2010 (Jul. 20, 2010). pp. 55-60.

(Continued)

*Primary Examiner* — Paul W Dickinson
(74) *Attorney, Agent, or Firm* — Katten Muchin Rosenman LLP

(57) ABSTRACT

The invention relates to biocompatible polysaccharide-based nanocapsule templated on oil core of diameter not exceeding 1 μm, stabilized without low molecular weight surfactants. The nanocapsule shows long-term stability in an aqueous suspension and is able to highly efficient encapsulation of hydrophobic compounds.

10 Claims, 13 Drawing Sheets

Number-weighted size distribution of capsules Hy-C6 templated on oleic acid cores at different time after preparation.

(56) References Cited

PUBLICATIONS

Nan Zhang et al: Polysaccharide-Based Micelles for Drug Delivery. Pharmaceutics. vol. 5. No. 2. May 27, 2013 (May 27, 2013). pp. 329-352.
Di Cui et al: 11 Hydrophobic Shell Loading of Biopolyelectrolyte Capsules. Advanced Materials. vol. 23. No. 24. Jun. 24, 2011 (Jun. 24, 2011) pp. H200-H204.
International Search Report/Written Opinion dated Oct. 10, 2016.

* cited by examiner

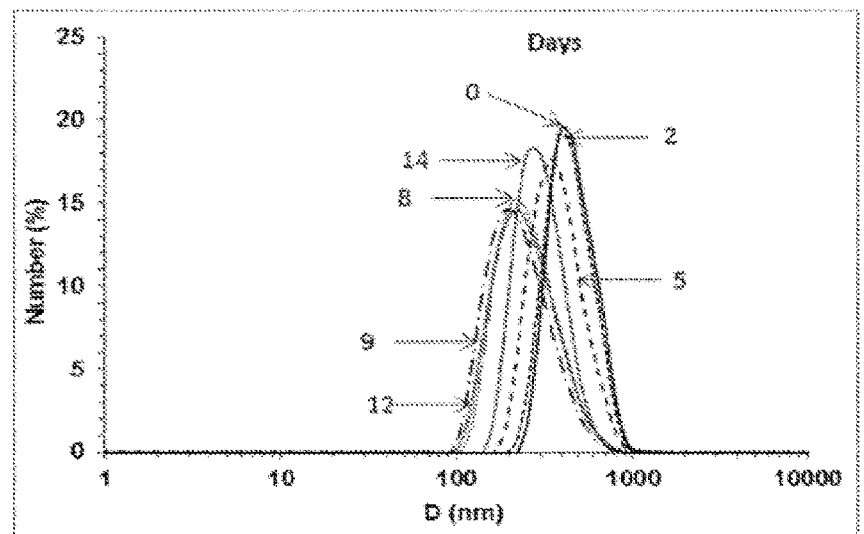
Fig. 1 Number-weighted size distribution of capsules Hy-C6 templated on oleic acid cores at different time after preparation.
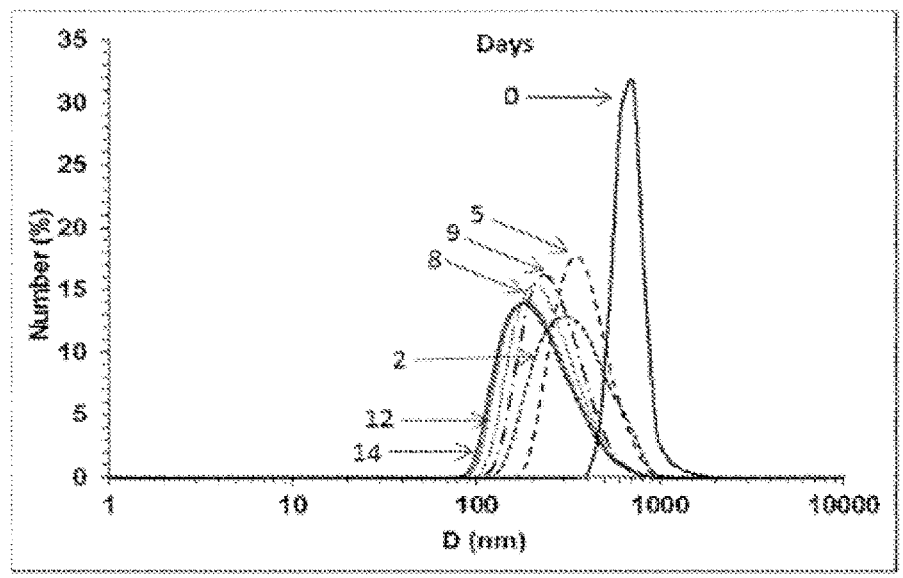
Fig. 2 Number-weighted size distribution of capsules Hy-C8 templated on oleic acid cores at different time after preparation.

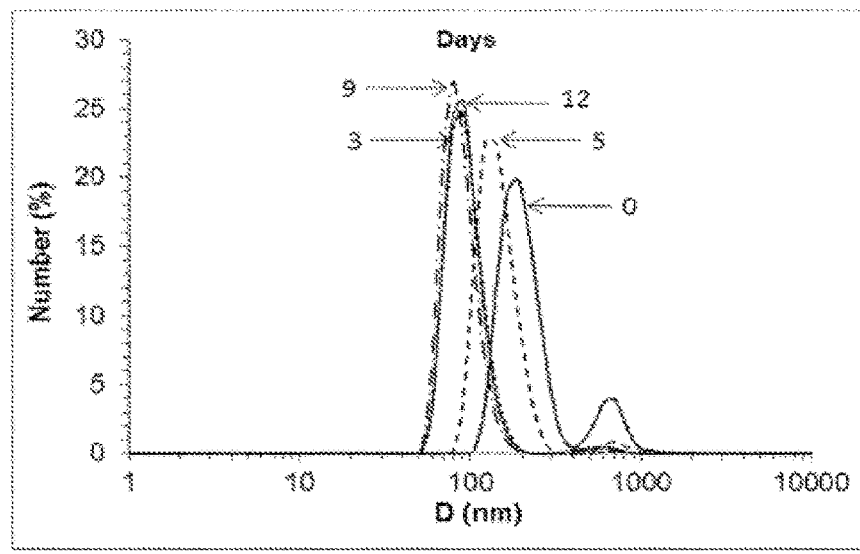
Fig. 3 Number-weighted size distribution of capsules Hy-C12 templated on oleic acid cores at different time after preparation.
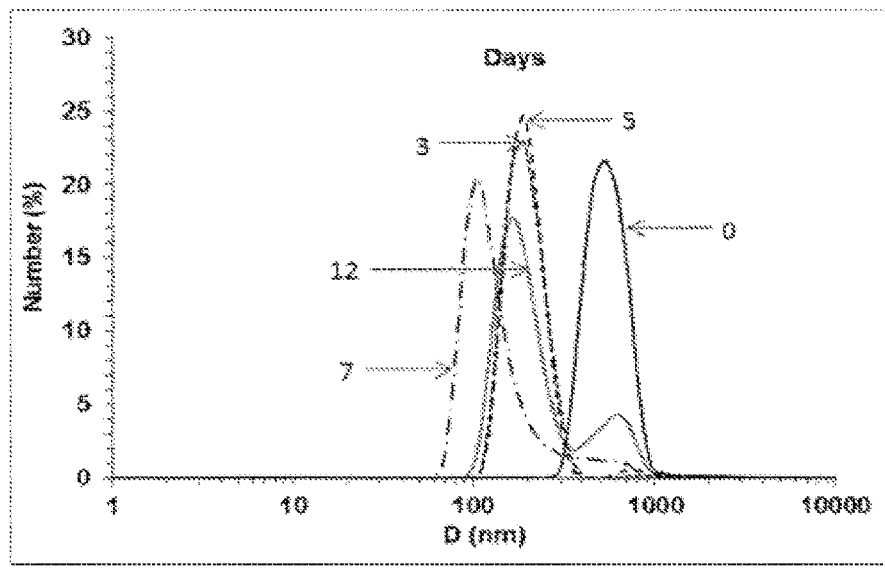
Fig. 4 Number-weighted size distribution of capsules Hy-C18 templated on oleic acid cores at different time after preparation.

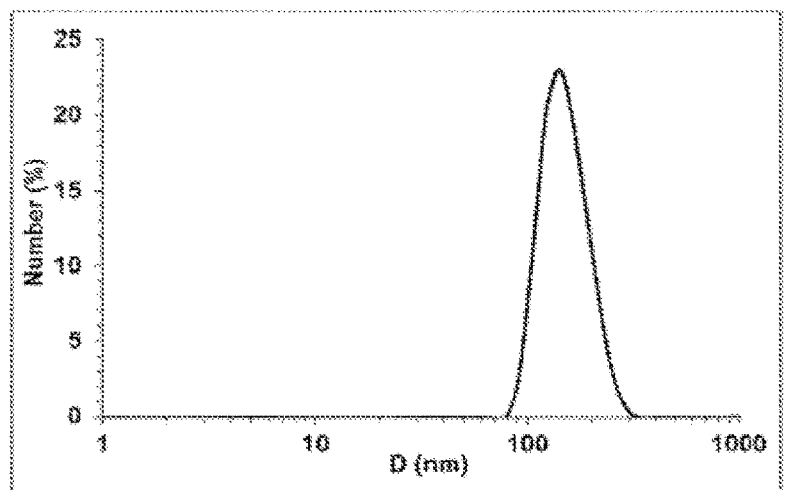
Fig. 5 Number-weighted size distribution of capsules templated on oleic acid cores stabilized by dodecyl derivative of hyaluronic acid (c=5 g/L).
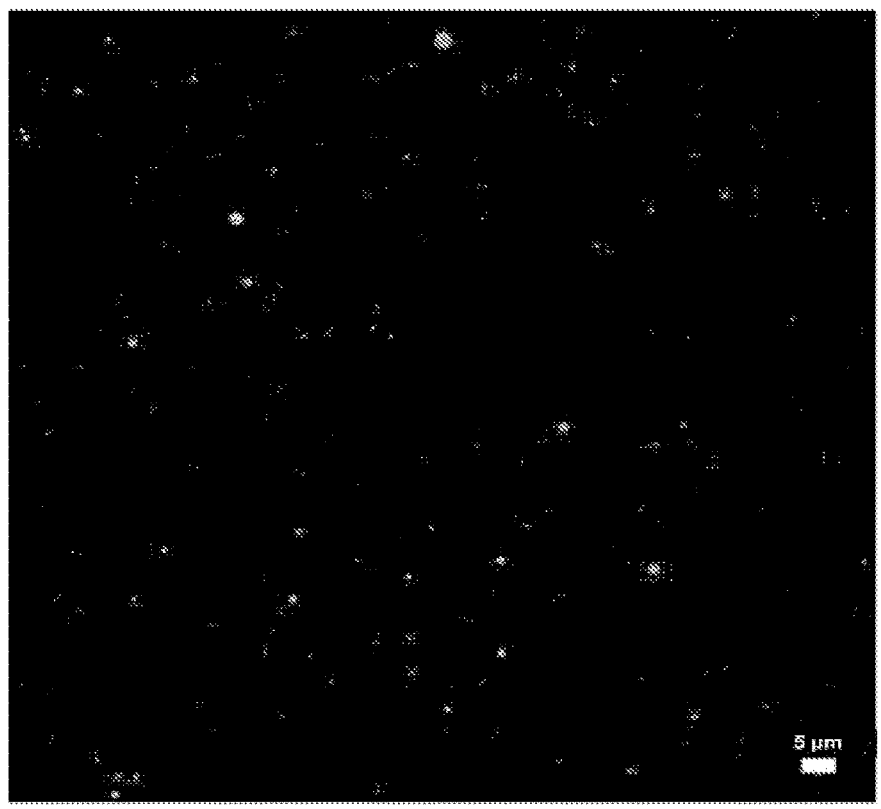
Fig. 6 Confocal micrograph of capsules Hy-C12 templated on oleic acid core with encapsulated Nile red (c=0.15 g/L). Laser 488 nm, scale bar 5μm.

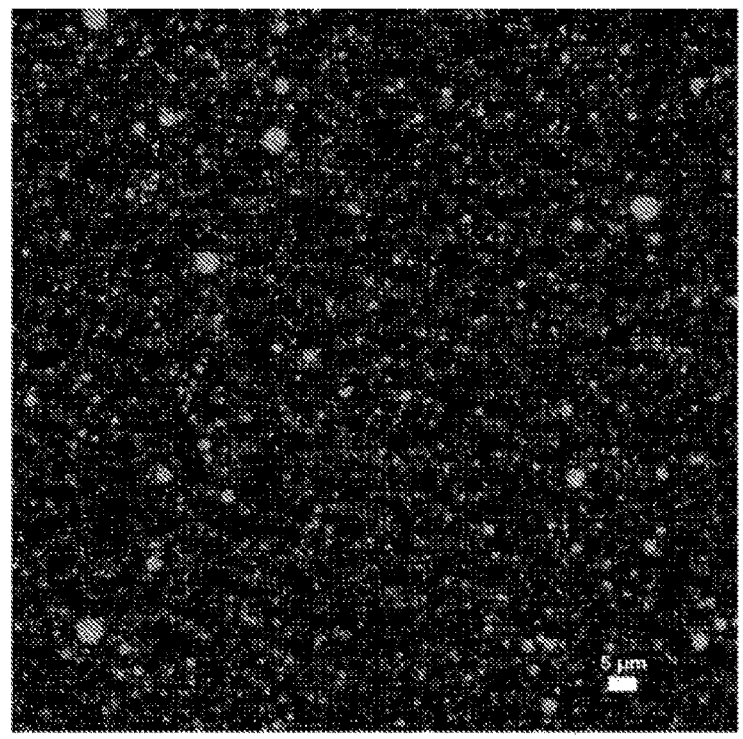
Fig. 7 Confocal micrograph of capsules Hy-C12 templated on oleic acid core with encapsulated Nile red (c=1 g/L). Laser 488 nm, scale bar 5μm.
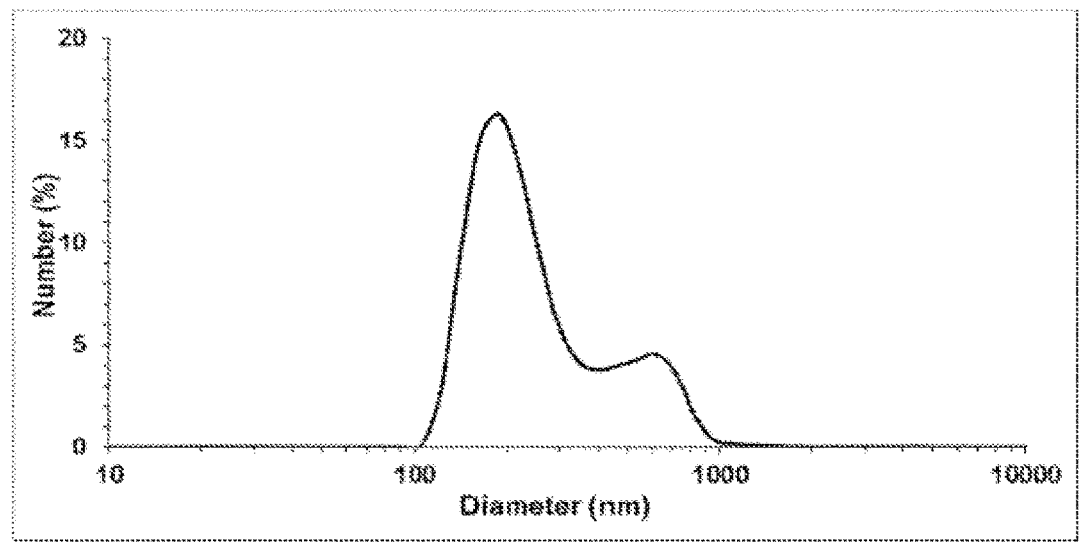
Fig. 8 Number-weighted size distribution of Hy-C12 capsules templated on oleic acid with encapsulated Nile red (c=0.15 g/L).

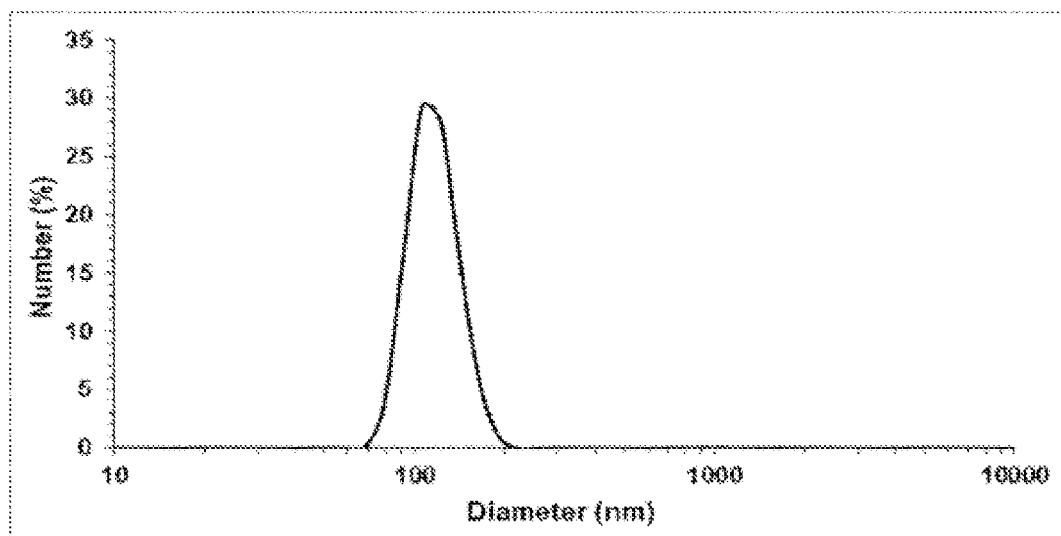
Fig. 9 Number-weighted size distribution of Hy-C12 capsules templated on oleic acid with encapsulated perylene (c=0.15 g/L).
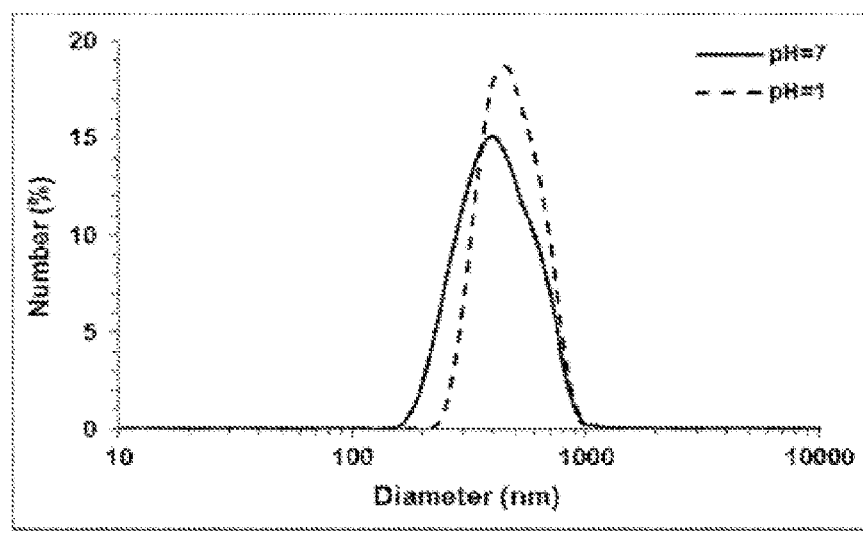
Fig. 10 Number-weighted size distribution of Hy-C12 capsules templated on oleic acid before and after acidification of the suspension.

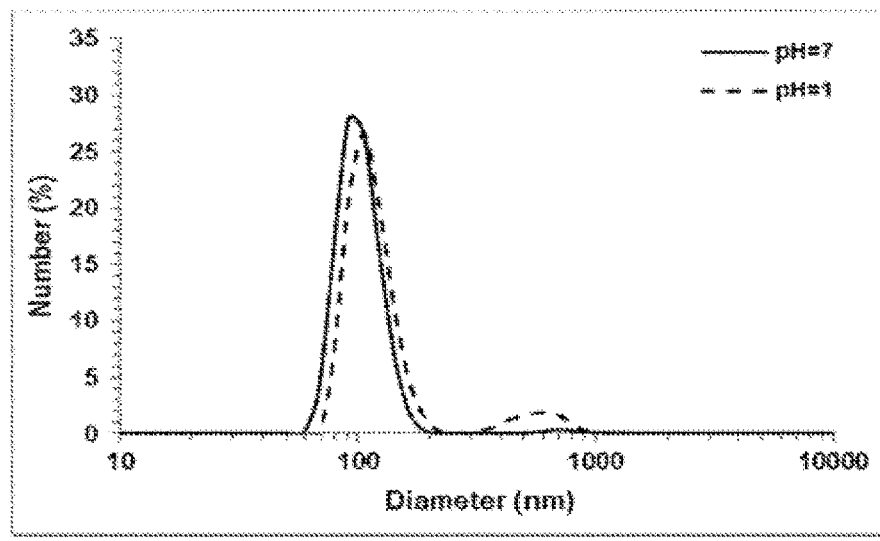
Fig. 11 Number-weighted size distribution of Hy-C18 capsules templated on oleic acid before and after acidification of the suspension.
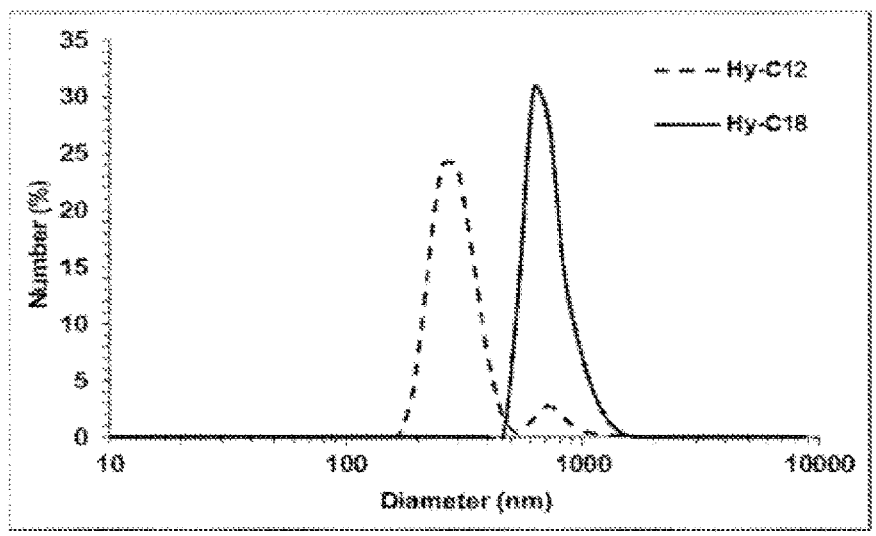
Fig. 12 Number-weighted size distribution of capsules templated on linseed oil cores stabilized by Hy-C12 and Hy-C18 capsules, respectively.

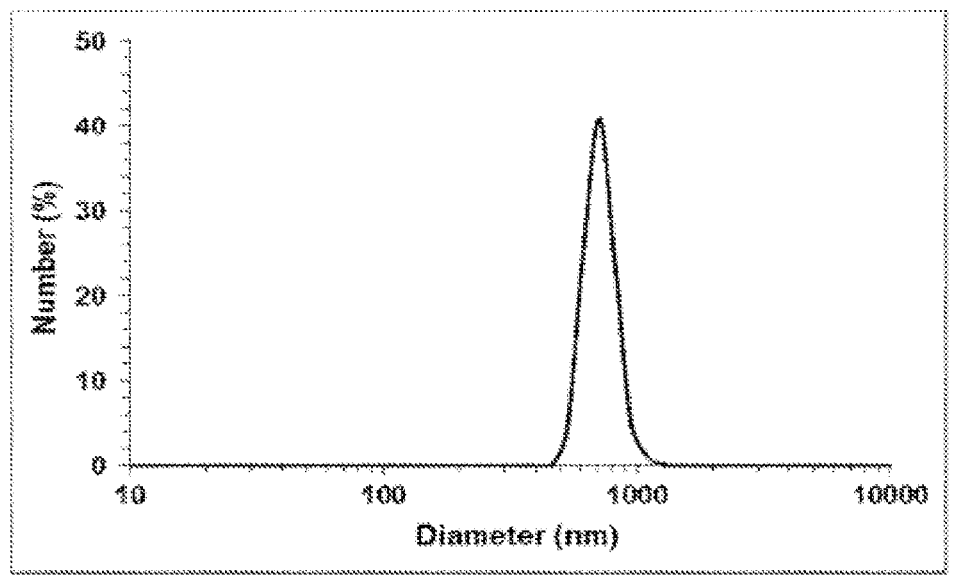
Fig. 13 Number-weighted size distribution of Hy-C12 capsules templated on argan oil cores.
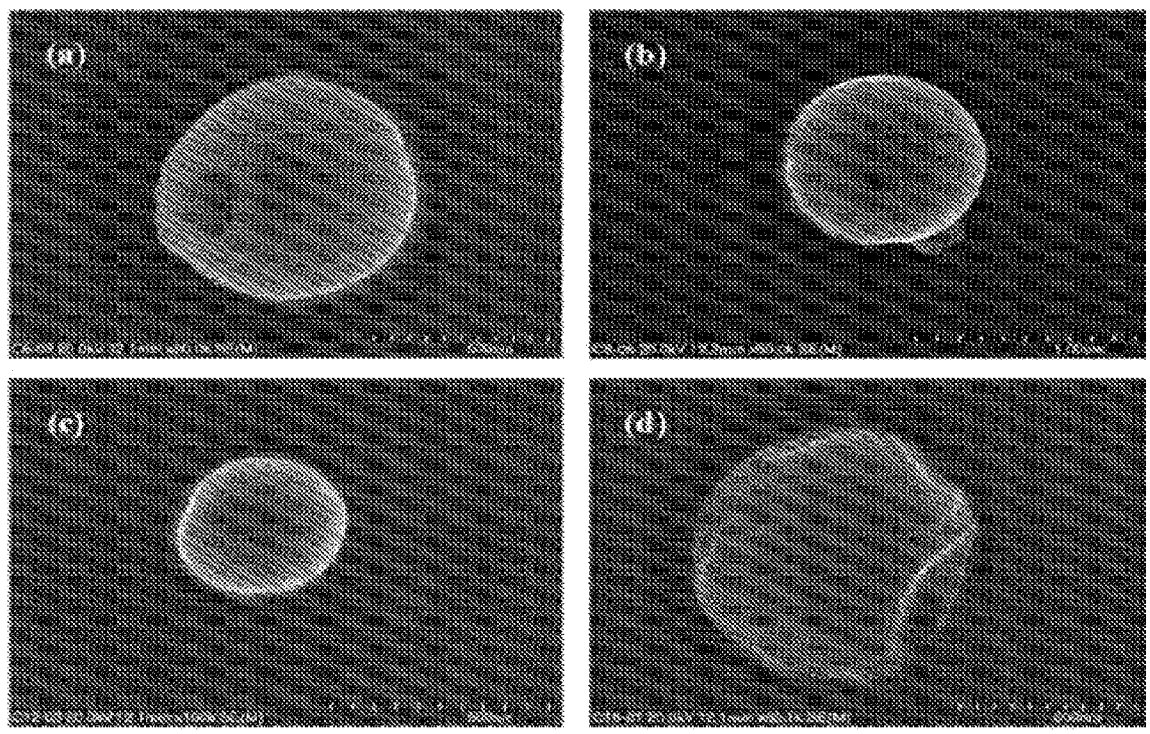
Fig. 14 SEM images of capsules templated on n-octadecane cores stabilized by Hy-C6 (a), Hy-C8 (b), Hy-C12 (c) and Hy-C18 (d), respectively.

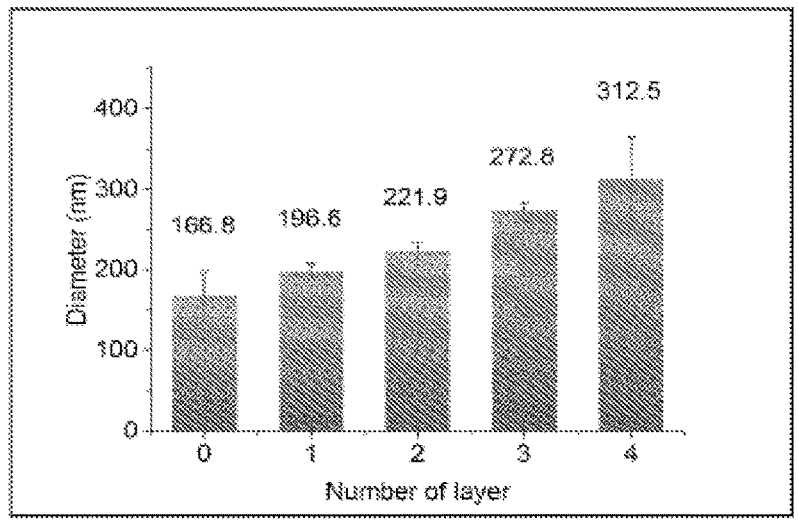
Fig. 15 Number-weighted size of capsules Hy-C12 templated on oleic acid cores as a function of number of layers of cationically and anionically modified chitosan (c=1 g/L).
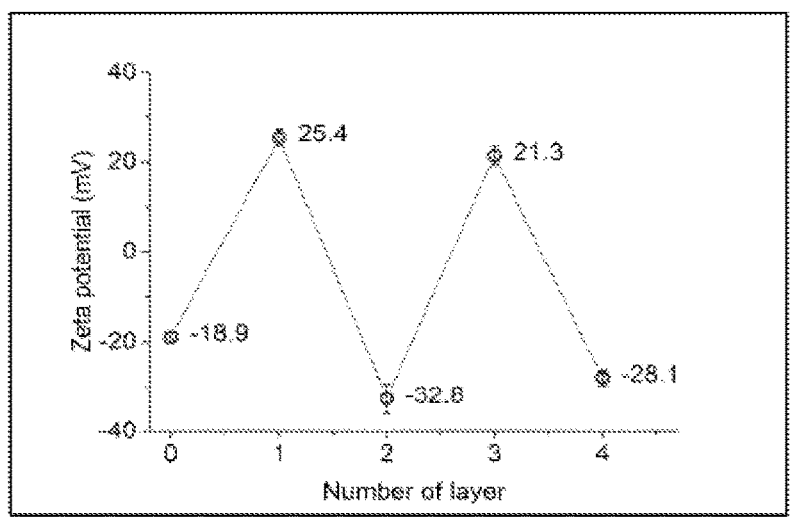
Fig. 16 Zeta potential of capsules Hy-C12 templated on oleic acid cores as a function of number of layers of cationically and anionically modified chitosan (c=1 g/L).

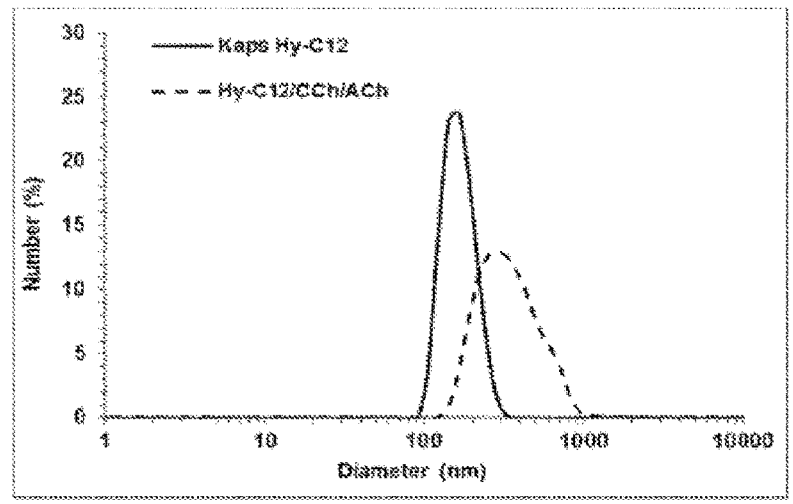

Fig. 17 Number-weighted size distribution of capsules Hy-C12 templated on oleic acid cores covered by one bilayer of cationically and anionically modified chitosan (CCh and ACh, respectively, c=10 g/L).

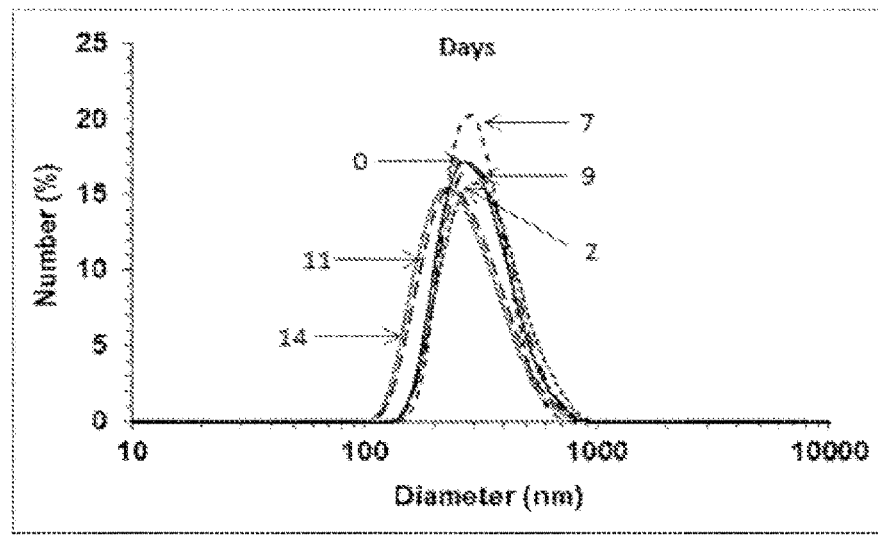

Fig. 18 Number-weighted size distribution of capsules templated on oleic acid cores stabilized by dodecyl derivative of cationically modified chitosan (CChit-C12) at different times after preparation thereof (DLS measurements).

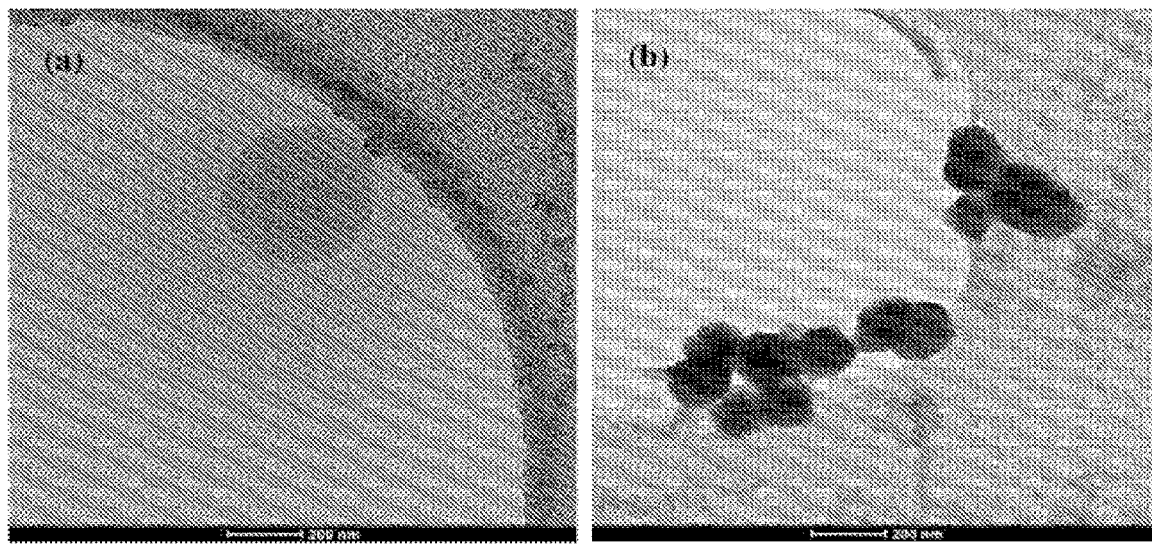

Fig. 19 Cryo-TEM images of capsules templated on oleic acid cores stabilized by dodecyl derivative of cationically modified chitosan (CChit-C12), not stained (a) and stained with phosphotungstic acid (b).

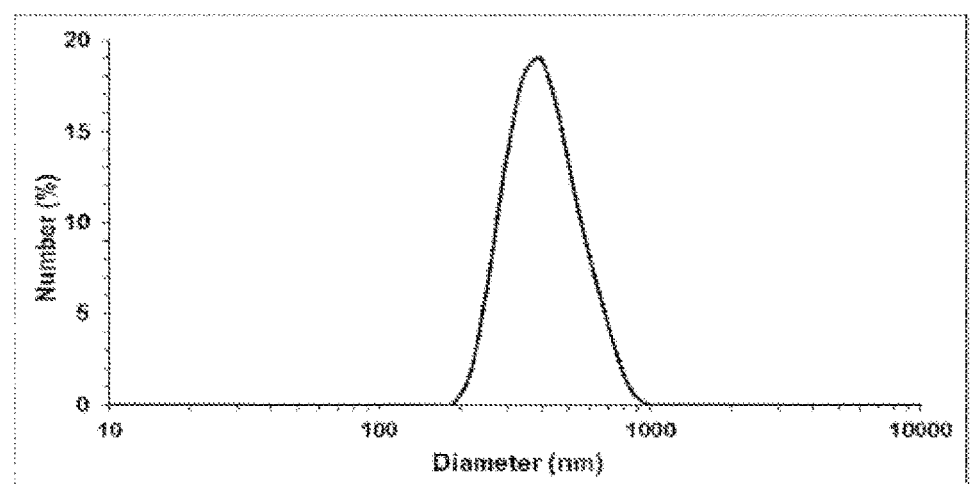

Fig. 20 Number-weighted size distribution of capsules templated on oleic acid cores stabilized by dodecyl derivative of cationically modified chitosan (CChit-C12) dissolved in 0.12 M acetic acid.

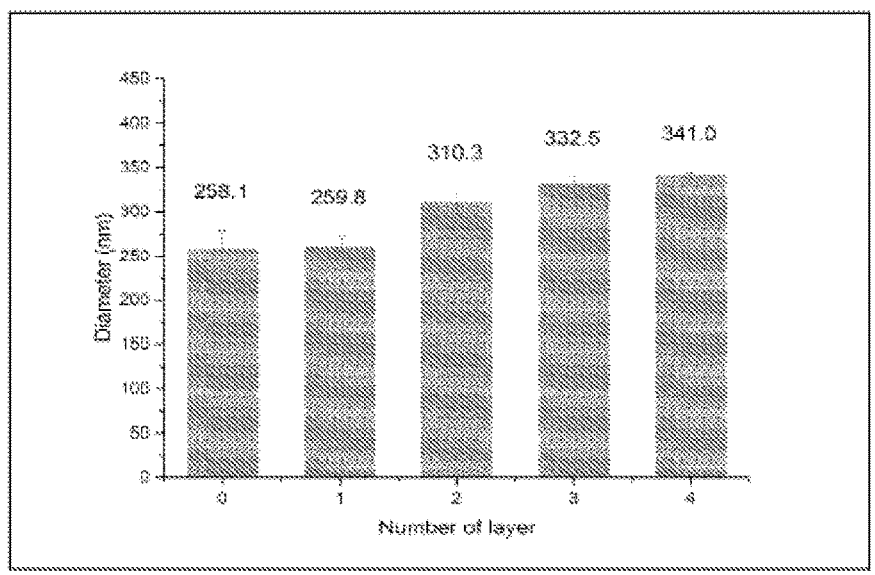
Fig. 21 Number-weighted size of capsules CChit-C12 templated on oleic acid cores as a function of number of layers of cationically and anionically modified chitosan (c=1 g/L).
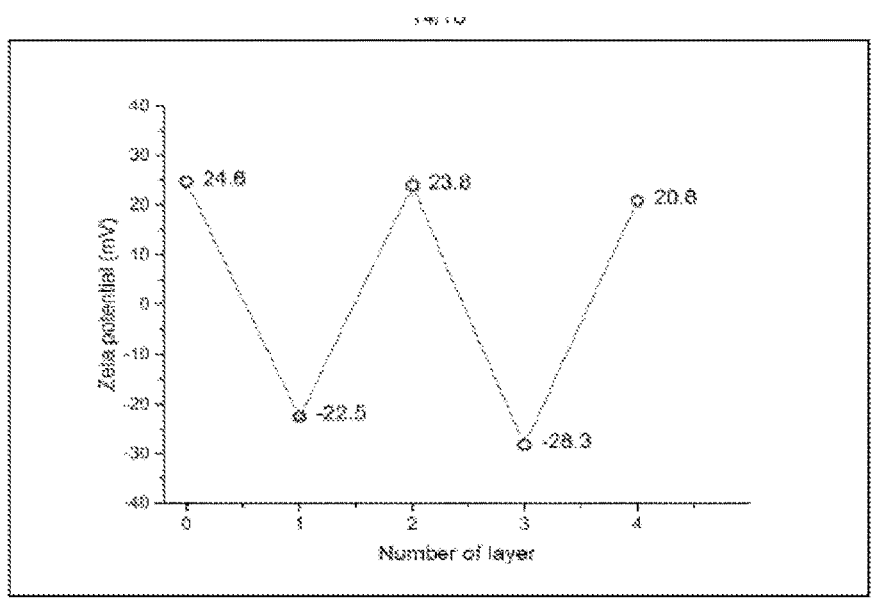
Fig. 22 Zeta potential of capsules CChit-C12 templated on oleic acid cores as a function of number of layers of cationically and anionically modified chitosan (c=1 g/L).

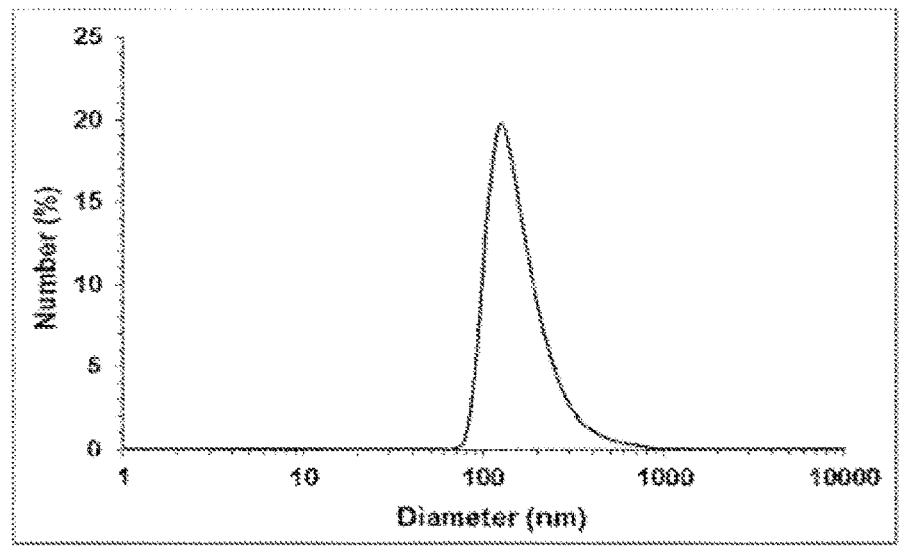

Fig. 23 Number-weighted size distribution of capsules templated on oleic acid cores stabilized by anionically modified octadecyl derivative of chitosan oligosaccharide (oChit-C18-sulf).

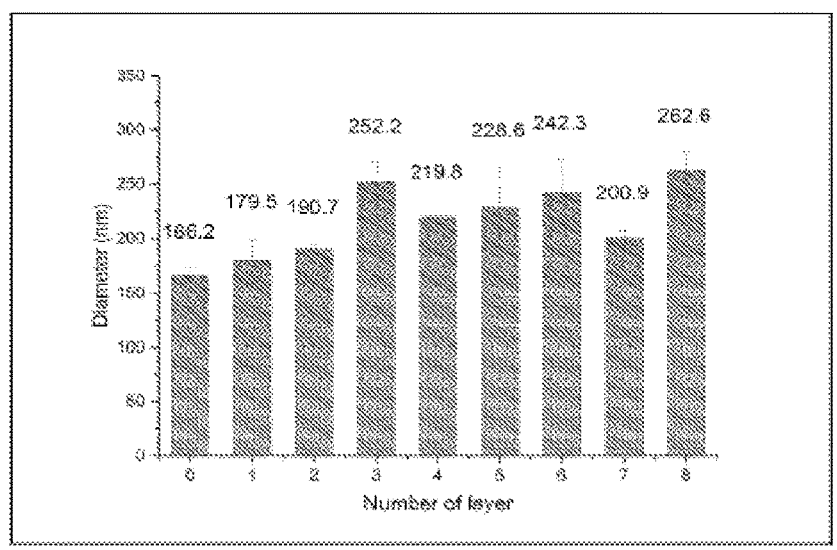

Fig. 24 Number-weighted size of capsules templated on oleic acid cores stabilized by anionically modified octadecyl derivative of chitosan oligosaccharide (oChit-C18-sulf) as a function of number of layers of cationically and anionically modified chitosan (c=1 g/L).

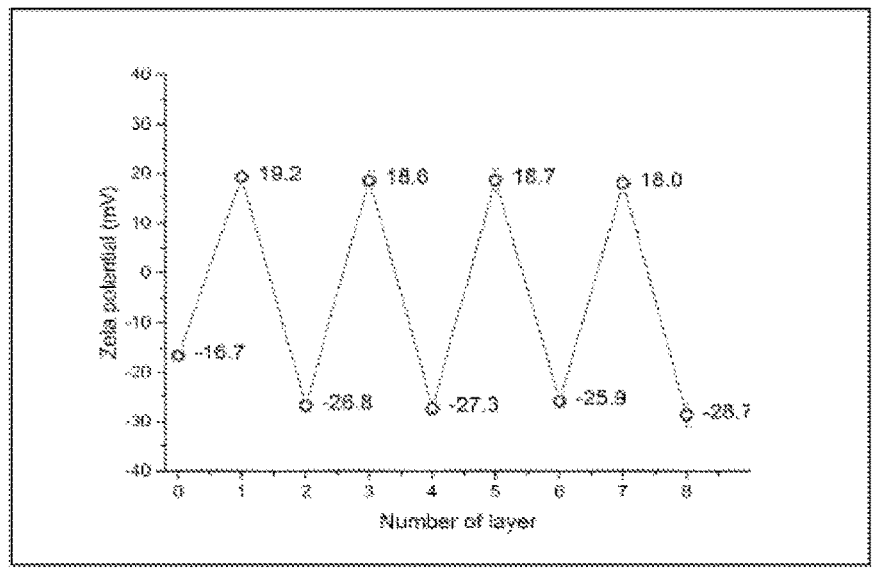

Fig. 25 Zeta potential of capsules templated on oleic acid cores stabilized by anionically modified octadecyl derivative of chitosan oligosaccharide (oChit-C18-sulf) as a function of number of layers of cationically and anionically modified chitosan (c=1 g/L).

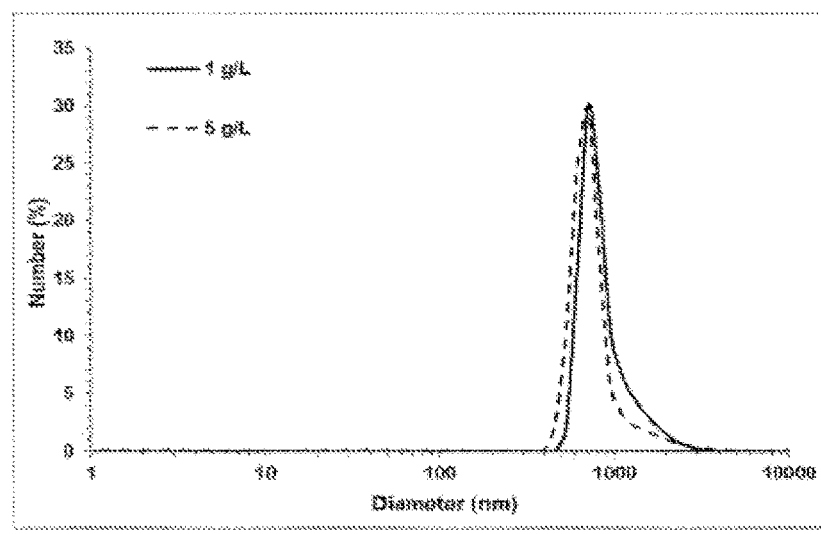

Fig. 26 Number-weighted size distribution of capsules templated on oleic acid cores stabilized by octadecyl derivative of hyaluronic acid Hy-C18x (4.5% of substitution), concentration c= 1 g/L and 5 g/L, respectively.

NANOCAPSULE FOR DELIVERY OF LIPOPHILIC COMPOUND AND PROCESS OF PREPARATION THEREOF

CROSS-REFERENCE TO RELATED APPLICATIONS

This application is a 371 U.S. National Stage of International Application No. PCT/PL2016/050032, filed Jul. 12, 2016 and published in English as WO 2017/014655 A1 on Jan. 26, 2017, which claims the benefit of and priority to Polish Patent Application No. P.413155, filed Jul. 17, 2015. The entire disclosures of the above applications are incorporated herein by reference.

FIELD OF THE INVENTION

The invention relates to biocompatible polysaccharide-based capsules templated on liquid cores of diameter below 1 μm, stabilized by hydrophobically modified charged polysaccharides without low molecular weight surfactants, able to efficiently encapsulate hydrophobic compounds and having long-term stability in aqueous suspension and process of preparation and stabilization thereof.

BACKGROUND OF THE INVENTION

Stable and biodegradable oil-in-water nanoemulsion (O/W) is one of the most common type of nanoformulation used as delivery system of various active compounds, particularly drugs, vitamins, hormones, dyes, antioxidants, pesticides, Magnetic Resonance Imaging (MRI) and Positron emission tomography (PET) contrast agents. The main goal of such carriers is to improve operational efficiency of the encapsulated compounds through their protection against degradation, reduction of toxicity by decreasing the adverse effects towards body tissues.

Ultrasound or mechanically-assisted homogenization of two immiscible phases leads to formation of oil-in-water emulsions. While the process seems to be very simple, it is a great challenge to obtain stable droplets. It is due to the thermodynamic instability of nanoemulsions which require usage of stabilizers to improve stability of oil droplets in polar media. Surface-active agents (surfactants) are commonly used to stabilize oil droplets as they are able to adsorb at the water/oil interface leading to the reduction of the surface tension. It causes a disruption of the droplet surface, reduction of their sizes and prevents their aggregation due to the e.g. repulsive electrostatic forces.

Another strategy towards improvement of stability of nanoemulasions is implementation of layer by layer technique (LbL) leading to formation of ultrathin polymer films formed in a process of alternate adsorption of oppositely charged polyelectrolyte. The resulting structures are referred to nanocapsules templated on liquid cores. The use of low molecular weight ionic surfactants allows to cover the oil cores with polymer shells, however, the dynamic nature of interactions within micellar systems is a serious limitation. The most important drawback is that the excessive dilution of the system can result in reduction in surfactant concentration below the critical micelle concentration (CMC) leading to disintegration of the aggregate stabilizing the oil droplets and thus to uncontrolled release of encapsulated compounds before reaching the target. Another important point is the selection of an appropriate pair of surfactant and polyelectrolyte being the first layer of the shell as the formation of stable interfacial complex is crucial for formation of stable shell of the capsule [U. Bazylińska et al., Soft Matter, 2011, 7, 6113-6124; Bazylińska U. et al., Bioelectrochemistry, 2012, 87, 147-153].

While the use of block copolymers seems to be a solution to the problem of instability of micellar system due to the lower CMC value than for low molecular weight surfactants, variations in the environmental conditions also lead to destabilization of nanoformulation [L. I. Atanase et al., International Journal of Pharmaceutics, 2013, 448, 339-345]. It makes the materials resistant to changes in external parameters have been sought.

Amphiphilic graft copolymers enable to achieve aforementioned goals as they are able to anchor hydrophobic arms in the oil droplets ensuring their stabilization [F. Liu et al., Polymer Chemistry, 2014, 5, 1381-1392]. Those polymers play dual role in nanoemulsions, on the one hand they act as droplets stabilizers, on the other hand, they constitute the first layer of the shell. Moreover, the use of graft polyelectrolytes enables formation of multilayer capsules of enhanced stability [J. Szafraniec et al., Nanoscale, 2015, 7, 5525-5536].

Although the controlled or sustained release of cargo from different types of nanocarriers is of considerable interest in applications such as self-healing materials, nutrient preservation, marine industry or fragrance release, such an approach is particularly important in the field concerning lipophilic biologically active compounds of low biodistribution and poor pharmacokinetic profiles resulting from the hydrophobic character of such compounds. Bearing in mind that there is a wide range of molecules of different structures, molar masses and physicochemical properties (e.g. polarity or viscosity) it is clear that different alternatives for manufacturing the delivery systems need to be considered.

While numerous papers and patents have been devoted to nanoemulsions used as carriers of various compound in cosmetics, food industry, pharmacy or agriculture, among others, they are always stabilized by either low molecular weight surface-active agents or polymeric surfactants. See, for example:

U.S. Patent No. 20060063676 describes nanoemulsions encapsulating pesticides in oil cores stabilized by ionic or non-ionic surfactants.

U.S. Patent No. 2007036831 is directed to nanoemulsions having high anti-inflammatory properties, being stabilized by ionic and/or non-ionic surfactants.

It is important for biomedical applications of nanocapsules templated on liquid cores that they are resistant to concentration changes that may occur after intravenous administration. Uncontrolled release of encapsulated drug or contrast agent before reaching the target is highly unfavorable and may cause the adverse side effects. Biodegradable polymers of low toxicity such as poly(glutamic acid), polypeptides such as poly(L-lysine) and poly(L-arginine) as well as modified polysaccharides (e.g. chitosan and dextran) are used to minimize such a risk [A. Karabasz et al., Journal of Nanoparticles Research, 2014, 16, 1-14; R. Vecchione et al., Nanoscale, 2014, 6, 9300-9307], however, the oil cores of capsules are still stabilized by typical surface-active agents.

Publication No. WO9637232 describes technique of stabilization of oil droplet by interfacial complex formed between anionic phospholipid and cationic polysaccharide. Such capsules are directed towards delivery of biologically active agents such as indomethacin, metipranolol, diazepam and cyclosporine A.

Patent No. EP2266546 describes nanoemulsions templated on cores composed of saturated or unsaturated fatty acids having 12-24 carbon atoms in chains being stabilized by anionic phospholipids and covered by thin chitosan layer. Such capsuled were described as carriers of lipophilic compounds used in cosmetics and pharmacy.

Patent No. EP2266546 discloses formulations of diameter not exceeding 1 µm in which oil cores stabilized by lecithin and covered by chitosan, being able to efficient encapsulation of cyclosporine A.

Publication No. WO2013001124 describes technique of preparation of nanoemulsions templated on isoprenoids stabilized by anionic or non-ionic surfactants and covered by poly(D-glucosamine) that were used as carriers of vaccines.

Numerous inventions relying on stabilization of oil cores by block polymers acting as surfactants have been also disclosed in patents, for example:

Publication No. WO2015013566 discloses the technique of preparation of nanoemulsion stabilized by block copolymers such as polyethylene glycol and 1,2 distearoyl-sn-glycero-3-phosphoethanolamine used in cancer therapy as carriers of platinum(II) complex.

Russian Patent No. RU 2494728 describes nanocapsules templated on eucalyptus oil stabilized by block copolymer of poly(ethylene oxide) and poly(propylene oxide) (PEO-block-PPO) suspended in aqueous solution of polysaccharides (e.g. chitosan) being used as carriers of biologically active lipophilic compounds.

Although numerous papers and patents have been focused on preparation of nanoemulsion-based carriers, none of them describes synthesis of nanocapsules stabilized without classical surface-active agents composed of hydrophobic "head" and hydrophilic "tail". Such molecules adsorb at the interfacial surface one next to each other stabilizing droplet in polar medium, however dissolution make surfactant molecules leave the surface of the droplet what leads to their destabilization which is a significant drawback.

Unexpectedly, this problems have been solved in presented invention relying to nanoemulsion-based carriers of lipophilic compounds described according to claims presented below.

DETAILED DESCRIPTION OF THE INVENTION

The invention relates to novel biocompatible system of core-shell architecture and the process of preparation thereof. Nanocapsules templated on liquid cores are stabilized by charged hydrophobically modified polysaccharides without the use of low molecular weight surfactants. Emulsion of droplets of diameter below 1 µm is formed in ultrasound-assisted emulsification of an aqueous solution of modified polysaccharide (c=1-10 g/L) with appropriate amount of oil (1-10 v/v %). Such capsules are then covered by ultrathin polyelectrolytes' films what leads to enhancement in their stability, improvement of biocompatibility and pharmacokinetic profile of encapsulated compounds. Stability of such capsules is affected by both, type of polysaccharide as well as the type of introduced modification of the polysaccharide. Thus, appropriate balance between content and length of hydrophobic side chains needs to be found. It is known that too short hydrophobic arms do not provide sufficient stabilization of oil droplets while too high degree of hydrophobic modification leads to decrease in solubility of polysaccharides what significantly limits their application.

In particularly preferred embodiments of the invention, hydrophobically modified ionic oligo- and polysaccharides such as chitosan, chitosan oligosaccharide, dextran, carrageenan, amylose, starch, hydroxypropyl cellulose, pullulan and glycosaminoglycans (e.g. hyaluronic acid, heparan sulfate, heparin sulfate, keratan sulfate, chondroitin sulfate, dermatan sulfate) and their derivatives are claimed. The most suitable stabilizers are believed to be hyaluronic acid, chitosan and chitosan oligosaccharide derivatives.

Any polysaccharide can be hydrophobically modified. Preferably, molar mass of polysaccharide used as emulsion stabilizer should exceed 2000 g/mol, however the most suitable are polysaccharides of molar mass above 5000 g/mol.

In particularly preferred embodiments of the invention, polysaccharides used as emulsion stabilizers should possess stable electrostatic charge provided by ionic groups within polymeric chains, such as carboxylic, sulfonic, sulfate, phosphate, ammonium, pyridine or phosphono groups. Preferably, the content of ionic groups should not be less than 10%, more suitable it should exceed 40%, while the most suitable for good stabilization of emulsion droplets it to use polymers having at least 60% of ionic groups.

In particularly preferred embodiments of the invention, stabilization of oil cores of the capsules can be provided by polysaccharides modified with hydrophobic groups of either linear or branched alkyl chains having 3-30 carbon atoms being single or/and multiple-bounded. It is also acceptable to use cyclic compounds and/or aromatic compounds as hydrophobic side chains that may also contain weakly polar groups such as ether or disulfide groups or halogens. Preferably, the degree of substitution of hydrophobic chains into polysaccharide molecules should not exceed 40%. To achieve good solubility in water less than 10% of substitution of hydrophobic groups is recommended, however in order to provide the best stabilization of oil cores of capsules it should not exceed 5%. It is recommended to use hydrophobic compounds having 6-18 carbon atoms, however the most suitable is to use 12-carbon side chains.

TABLE 1

Characteristics of polysaccharides used for stabilization of the emulsion.

| | Polysaccharide and its molar mass | Type of modification | Abbreviation | Degree of substitution[a] |
|---|---|---|---|---|
| 1 | Hyaluronic acid | Hexyl groups | Hy-C6 | 2.0% |
| 2 | ($M_n \approx$ 200000 g/mol) | Octyl groups | Hy-C8 | 2.0% |
| 3 | | Dodecyl groups | Hy-C12 | 4.5% |
| 4 | | Octadecyl groups | Hy-C18 | 1.5% |
| 5 | | | Hy-C18x | 4.5% |
| 6 | Chitosan (Mv < 150000 g/mol) | Dodecyl groups | CChit-C12[b] | 2.0% |
| 7 | Chitosan oligosaccharide ($M_n \approx$ 5000 g/mol) | Octadecyl groups | oCh-C18-sulf[c] | 1.5% |

[a]Calculated based on elemental analysis.
[b]Cationically modified chitosan, 67.5% of GTMAC substitution.
[c]Anionically modified chitosan oligosaccharide, 61.5% of sulfonic groups substitution.

Throughout the specification the polysaccharides represented by the abbreviations "Hy-C18" and "Hy-C18x" represent different moieties and the "x" in "Hy-C18x" does not represent a variable.

In particularly preferred embodiments of the invention, ultrasound-assisted process is used to obtain nanoemulsions: sonication should be carried out for 15-120 minutes at temperature between 4-40° C. Preferably, it should last 30-60 minutes at 20-35° C., however the most suitable conditions providing preparation of nanocapsules are: 30-minute sonication performed at room temperature.

Polysaccharide-based nanocapsules are manufactured using aqueous solution of hydrophobically modified polysaccharide at pH 2-12, concentration varying between 0.1-30 g/L and ionic strength between 0.001 M and 3 M. Preferably, the ionic strength of the solution of polysaccharides should be in the range of 0.015-0.15 M and concentration between 1-10 g/L.

Oil cores of invented capsules are composed of non-toxic hydrophobic compounds, either natural or synthetic, such as oleic acid, isopropyl palmitate, PROVINOL, fatty acids and pure natural oils (both, vegetable and animal origin) or mixtures thereof including linseed oil, soybean oil, argan oil, among others. The resulting capsules have a wide range of applications such as carriers of lipophilic compounds of low bioavailability or nanoreactors for enzymatic and/or biological processes. Lipophilic active compounds and substrates for enzymatic reactions may be either core material or compound dissolver therein. Mixing delivered lipophilic compounds with oil phase at the first stage of the process of preparation of capsules minimizes the risk of damage of vulnerable molecules and ensures high encapsulation efficiency.

Dissolving of dyes in oil cores leads to formation of capsules that can be easily microscopically imaged and studied in order to determine the release profiles of cargo from the cores. The concentrations of encapsulated dyes vary in the range of approx. $10^{-5}$ M up to concentrations obtained for saturated solutions.

Capsules used for bioimaging should encapsulate dyes for which excitation and emission wavelength are in the red part of the spectrum, since it facilitates in vivo visualization as the emission of the dye does not overlap with the autofluorescence of cells.

In particularly preferred embodiments of the invention, invented nanocapsules should be coated with ultrathin films of polyelectrolytes. Particularly preferred is the use of biocompatible polyelectrolytes and their derivatives of natural origin including chitosan derivatives, dextran, starch, hydroksypropyl cellulose, glycosaminoglycans (including hyaluronic acid derivatives, heparin, heparan sulfate, keratan sulfate, chondroitin and dermatan), carrageenan, alginate and synthetic polyelectrolytes such as poly-L-lysine, poly-ornityne, poly (D-glutamic acid), derivatives of poly (lactic acid), polystyrenesulfonate, poly (diallildimethylammonium chloride), polyallylamine hydrochloride or polyethyleneimine. Fluorescently labelled polysaccharides are recommended in order to manufacture multilayer capsules for in vivo imaging.

Covering capsules with multilayer films is of crucial importance as it enables to control the charge of capsules and thus avoid aggregation of the product with blood cells what is essential for biomedical applications. Moreover, such strategy provides an increase in stability of the capsules as well as improvement of their bioavailability and biocompatibility. Preferably, the outer layer of the capsules should be anionically charged. It is particularly preferred to use an anionic derivative of chitosan and glycosaminoglycans. It is also recommended to modify the outer layer of the capsules with polyethylene glycol (PEG) as it results in an improvement of bioavailability of the capsules and prolongation of circulation time in the bloodstream.

An advantage of the invention is the possibility of preparation of biocompatible, stable nanoemulsion without the use of low molecular weight surfactant. Invented capsules can encapsulate hydrophobic compounds that are dissolved directly in the oil cores that provides highly efficient encapsulation. The simplicity of preparation, low energy and financial inputs in the production process, resistance to changes in environmental parameters (such as pH and concentration) and low complexity of biocompatible system allows it to be widely used as carriers of lipophilic biologically active compounds.

BRIEF DESCRIPTION OF THE DRAWINGS AND TABLES

Table 1 contains characteristics of polysaccharides used for stabilization of the emulsion.

Tables 2 and 3 contain data on stability of the capsules described in examples I-IV.

Table 4 shows how pH affects the morphology and stability of the capsules described in examples VIII-IX.

Table 5 includes data on parameters of the capsules templated on various types of oil cores as described in examples X-XII.

Table 6 contains data on stability of the capsules described in example XVI.

FIG. 1-4 show size distribution of capsules described in examples I-VI.

FIG. 5 is size distribution of capsules described in example V.

FIG. 6 and 7 show confocal micrographs of the capsules presented in examples VI i VII.

FIG. 8 is size distribution of capsules described in example VII.

FIG. 9 is size distribution of capsules described in example VII.

FIG. 10 and 11 show size distribution of capsules described in examples VIII-IX.

FIG. 12 shows size distribution of capsules described in examples X-XI.

FIG. 13 is size distribution of capsules described in example XII.

FIG. 14 shows SEM micrographs of the capsules templated on n-dodecane core described in example XIII FIG. 15 and 16 show size and zeta potential of the capsules covered by cationically and anionically chitosan as presented in example XIV.

FIG. 17 is size distribution of capsules described in example XV.

FIG. 18 is size distribution of capsules described in example XVI.

FIG. 19 is cryo-TEM micrograph of the capsules described in example XVI.

FIG. 20 is size distribution of capsules described in example XVII.

FIG. 21 and 22 show size and zeta potential of the capsules described in example XVIII.

FIG. 23 is size distribution of capsules described in example XIX.

FIG. 24 and 25 show size and zeta potential of the capsules described in example XX.

FIG. 26 is size distribution of capsules described in example XXI.

The invention has been described in detail and illustrated with particular reference to certain preferred embodiments thereof according to the following examples.

Example I Preparation of Nanocapsules Templated on Oleic Acid Cores Stabilized by Hyaluronic Acid Modified with Hexylamine Hyaluronic acid modified with hexyl side chains (Hy-C6) was dissolved in 0.1 M NaCl (1 g/L) and mixed with oleic acid (100:1 v/v). Both phases were vortexed for 5 minutes and emulsified for 30 minutes at room temperature in ultrasonic bath (540 W, 1-second pulse, 2-second break). Size of the resulted capsules was determined using dynamic light scattering technique (DLS) to be ca. 500 nm. The obtained capsules showed at least 2-week stability as confirmed by hydrodynamic diameter as well as zeta potential measurements. Two days after preparation a decrease in particle size was observed (to ca. 360 nm) what suggests destabilization of the aggregates and/or bigger capsules and formation of an emulsion containing only smaller and more stable particles (FIG. 1, Table 2).

Example II Preparation of Nanocapsules Templated on Oleic Acid Cores Stabilized by Hyaluronic Acid Modified with Octylamine Mixture of an aqueous solution of hyaluronic acid modified with octyl side chains (Hy-C8) and oleic acid was prepared according to the procedure described in Example I. Size of the resulted capsules was determined using dynamic light scattering technique (DLS) to be ca. 700 nm. The obtained capsules showed at least 2-week stability as confirmed by hydrodynamic diameter as well as zeta potential measurements. Two days after sonication significant decrease in particle size was observed (to ca. 300 nm) what suggests destabilization of the aggregates and/or bigger capsules and formation of an emulsion containing only smaller and more stable ones. (FIG. 2, Table 2).

Example III Preparation of Nanocapsules Templated on Oleic Acid Cores Stabilized by Hyaluronic Acid Modified with Dodecylamine Hyaluronic acid modified with dodecyl side chains (Hy-C12) was dissolved in 0.1 M NaCl (1 g/L) and mixed vigorously for 60 minutes using magnetic stirrer (500 rpm) in order to provide complete dissolution of the polysaccharide. Such an aqueous solution was then mixed with oleic acid (100:1 v/v), vortexed for 5 minutes and emulsified for 30 minutes at room temperature in ultrasonic bath (540 W, 1-second pulse, 2-second break). Size of the resulted capsules was determined using dynamic light scattering technique (DLS) to be ca. 200 nm. The obtained capsules showed at least 2-week stability as confirmed by hydrodynamic diameter as well as zeta potential measurements. As the size of resulted capsules decreased slightly after 3 days following sonication, destabilization of aggregates and/or bigger capsules of and formation of an emulsion containing only smaller and more stable particles is postulated. (FIG. 3, Table 3).

Example IV Preparation of Nanocapsules Templated on Oleic Acid Cores Stabilized by Hyaluronic Acid Modified with Octadecylamine Mixture of an aqueous solution of hyaluronic acid modified with octadecyl side chains (Hy-C18) and oleic acid was prepared according to the procedure described in Example III. Size of the resulted capsules was determined using dynamic light scattering technique (DLS) to be ca. 320 nm. The obtained capsules showed at least 2-week stability as confirmed by hydrodynamic diameter as well as zeta potential measurements. As the size of resulted capsules decreased to ca. 250 nm after 3 days following sonication destabilization of aggregates and/or bigger capsules of and formation of an emulsion containing only smaller and more stable particles is postulated (FIG. 4, Table 3).

Example V Determination of the Effect of Concentration of Polysaccharide and Saline on the Size and Stability of Capsules Templated on Oleic Acid Cores Stabilized by Hy-C12

Hyaluronic acid modified with dodecyl side chains dissolved in 0.15 M NaCl (5 g/L) was used to prepare nanocapsules templated on oleic acid cores according to procedure described in Example III. Size of the resulted capsules was determined using dynamic light scattering technique (DLS) to be ca. 280 nm (FIG. 5).

Example VI Determination of the Efficiency of Encapsulation of Hydrophobic Dye by Capsules Hy-C12 Templated on Oleic Acid Cores Mixture of an aqueous solution of hyaluronic acid modified with dodecyl side chains (Hy-C12) and oleic acid was prepared according to slightly modified procedure described in Example V—Nile red was dissolved in oleic acid (1 g/L) which was then mixed with an aqueous solution of Hy-C12. Size of the resulted capsules was determined using dynamic light scattering technique (DLS) to be ca. 320 nm. Moreover, confocal microscopy confirmed that the obtained capsules can efficiently encapsulate hydrophobic dyes (FIG. 6)

Example VII Determination of the Effect of Concentration of Encapsulated Dye on the Size and Stability of Capsules Mixture of an aqueous solution of hyaluronic acid modified with dodecyl side chains (Hy-C12) and oleic acid was prepared according to slightly modified procedure described in Example III—Nile red or perylene (0.15 g/L) were dissolved in oleic acid which was then mixed with an aqueous solution of Hy-C12. Size of the resulted capsules was determined using dynamic light scattering technique (DLS) to be ca. 190 nm and 120 nm for capsules with Nile red and perylene, respectively. Confocal microscopy was used in order to visualize capsules. The obtained results confirm that the capsules effectively encapsulate hydrophobic compounds dissolved in oil phase. (FIG. 7, FIG. 8, FIG. 9).

Example VIII Determination of the Effect of Low pH on Size and Stability of Capsules Hy-C12 Templated on Oleic Acid Cores Mixture of an aqueous solution of hyaluronic acid modified with dodecyl side chains (Hy-C12) and oleic acid was prepared according to slightly modified procedure described in Example III—suspension was acidified with 6 M HCl to pH=1.4. Size of the resulted capsules was determined using dynamic light scattering technique (DLS) to be ca. 280 nm before and 310 nm after acidification. Optical microscopy confirmed that decrease in pH of suspension does not affect the stability of capsules. (FIG. 10, Table 5).

Example IX Determination of the Effect of Low pH on Size and Stability of Capsules Hy-C18 Templated on Oleic Acid Cores Mixture of an aqueous solution of hyaluronic acid modified with octadecyl side chains (Hy-C18) and oleic acid was prepared according to procedure described in Example VIII. Size of the resulted capsules was determined using dynamic light scattering technique (DLS) to be ca. 125 nm before and 130 nm after acidification. Optical microscopy confirmed that decrease in pH of suspension does not affect the stability of capsules (FIG. 11, Table 5).

Example X Preparation of Nanocapsules Templated on Linseed Oil Cores Stabilized by Hyaluronic Acid Modified with Dodecylamine Mixture of an aqueous solution of hyaluronic acid modified with dodecyl side chains (Hy-C12) and linseed oil was prepared according to the procedure described in Example III. The resulted capsules were characterized using DLS: size was determined to be ca. 320 nm and zeta potential ca. −22 mV. The obtained results indicate that nanocapsules can be formed regardless the type of oil used as a core (FIG. 12, Table 6).

Example XI Preparation of Nanocapsules Templated on Linseed Oil Cores Stabilized by Hyaluronic Acid Modified with Octadecylamine Mixture of an aqueous solution of hyaluronic acid modified with octadecyl side chains (Hy-C18) and linseed oil was prepared according to the procedure described in Example X. The resulted capsules were characterized using DLS: size was determined to be ca. 530 nm and zeta potential ca. −21 mV. The obtained results indicate that nanocapsules can be formed regardless the type of oil used as a core (FIG. 12, Table 6)

Example XII Preparation of Nanocapsules Templated on Argan Oil Cores Stabilized by Hyaluronic Acid Modified with Dodecylamine Mixture of an aqueous solution of hyaluronic acid modified with dodecyl side chains (Hy-C12) and argan oil was prepared according to procedure described in Example X. The resulted capsules were characterized using DLS: size was determined to be ca. 710 nm and zeta potential ca. −20 mV. The obtained results indicate that nanocapsules can be formed regardless the type of oil used as a core (FIG. 13, Table 6).

Example XIII Preparation of Nanocapsules Templated on Solidified n-Octadecane Core for Scanning Electron Microscopy (SEM)

1 g/L solutions of hyaluronates (Hy-C6, Hy-C8, Hy-C12 and Hy-C18) in 0.1 M NaCl were vigorously mixed for 60 minutes in order to provide complete dissolution of polysaccharides. Solutions were heated up to ca. 35° C., mixed with n-octadecane (100:1 v/v) and emulsified for 30 minutes at 32° C. in ultrasonic bath (540 W, 1-second pulse, 2-second break). After cooling down the suspensions n-octadecane underwent solidification what significantly simplified imaging of capsules using scanning electron microscopy (FIG. 14).

Example XIV Formation of Multilayer Hy-C12 Capsules Templated on Oleic Acid Cores Capsules stabilized by hyaluronic acid modified with dodecyl side chains (Hy-C12) and templated on oleic acid cores were prepared according to procedure described in Example III. DLS measurements indicated formation of capsules of 170 nm in diameter and zeta potential equal to −19 mV. The resulted capsules were then covered by multilayer shells using layer by layer saturation technique— small quantities of either cationically or anionically modified chitosan (1 g/L in 0.15M NaCl) were added to suspension and after each step both, size of zeta potential were measured to control the process of adsorption of each layer. The resulted 4-layer-capsules were characterized to be 315 nm in diameter and have zeta potential equal to −28 mV. Gradual increase in average diameters of capsules as well as typical zigzag shape of the zeta potential plot confirms alternating adsorption of the polyelectrolytes and strong electrostatic stabilization of the capsules (FIGS. 15 and 16).

Interestingly, obtained results indicate that anionic layers are more preferred and provide better stabilization of capsules.

Example XV Determination of the Effect of Concentration of Polyelectrolyte on the Process of Preparation of Multilayer Hy-C12 Capsules Templated on Oleic Acid Cores Capsules stabilized by hyaluronic acid modified with dodecyl side chains (Hy-C12) and templated on oleic acid cores were prepared according to procedure described in Example III. DLS measurements indicated formation of capsules of 210 nm in diameter and zeta potential equal to −24 mV. The resulted capsules were then covered by multilayer shells using layer by layer saturation technique— small quantities of either cationically or anionically modified chitosan (10 g/L in 0.15M NaCl) were added to suspension and after each step both, size of zeta potential were measured to control the process of adsorption of each layer. The resulted 2-layer-capsules were characterized to be 240 nm in diameter and have zeta potential equal to −39 mV what indicates high stability of nanoemulsion (FIG. 17). By using concentrated chitosan solutions the dilution of the sample was minimized what is of significant importance for biomedical applications. Importantly, one bilayer of chitosan was sufficient to obtain system of stability higher than for capsules described in Example XIV. Moreover, obtained results confirmed that anionic layers are more preferred and provide better stabilization of capsules.

Example XVI Preparation of Nanocapsules Templated on Oleic Acid Cores Stabilized by Cationic Derivative of Chitosan Modified with Dodecyl Side Chains Cationic derivative of chitosan modified with dodecyl side chains (CChit-C12) was dissolved in 0.1 M NaCl (1 g/L) and vigorously mixed for 4 days in order to provide complete dissolution of polysaccharide. The resulted solution of CChit-C12 was mixed with oleic acid (100:1 v/v). Both phases were vortexed for 5 minutes and emulsified for 30 minutes at room temperature in ultrasonic bath (540 W, 1-second pulse, 2-second break). Size of the resulted capsules was determined using DLS to be ca. 320 nm. The obtained capsules showed at least 2-week stability confirmed by hydrodynamic diameter as well as zeta potential measurements. (FIG. 18, FIG. 19, Table 6).

Example XVII Determination of the Effect of Solvent on the Process of Preparation of CChit-C12 Nanocapsules Templated on Oleic Acid Cores Capsules stabilized by cationic derivative of chitosan modified with dodecyl side chains (CChit-C12) and templated on oleic acid cores were prepared according to modified procedure described in Example XVI—chitosan was dissolved in acetic acid (0.12 M) acetic acid. It resulted in decrease in time of dissolution of chitosan to less than 30 minutes. The resulted capsules were characterized to be 400 nm nm in diameter and have zeta potential equal to 25 mV (DLS measurements) (FIG. 20).

Example XVIII Preparation of Multilayer CChit-C12 Capsules Templated on Oleic Acid Cores Capsules stabilized by cationic derivative of chitosan modified with dodecyl side chains (CCHit-C12) and templated on oleic acid was prepared according to procedure described in Example XVI. The resulted capsules were characterized to be 260 nm in diameter and have zeta potential equal to +25 mV. The obtained capsules were then covered by multilayer shells using layer by layer saturation technique—small quantities of either cationically or anionically modified chitosan (1 g/L in 0.15M NaCl) were added to suspension and after each step both, size of zeta potential were measured to control the process of adsorption of each layer. The resulted 2-layer-capsules were characterized to be 340 nm in diameter and have zeta potential equal to +21 mV. Gradual increase in average diameters of capsules as well as typical zigzag shape of the zeta potential plot confirms alternating adsorption of the polyelectrolytes and strong electrostatic stabilization of the capsules (FIG. 21, FIG. 22). Moreover, obtained results confirmed that anionic layers are more preferred and provide better stabilization of capsules.

Example XIX Preparation of Capsules Templated on Oleic Acid Cores and Stabilized by Octadecyl Derivative of Anionically Modified Chitosan Oligocaccharide Capsules templated on oleic acid was prepared according to modified procedure described in Example I—octadecyl derivative of anionically modified chitosan oligocaccharide (oChit-C18-sulf) was used as emulsion stabilizer. The resulted capsules were characterized using DLS to be 150 nm in diameter (FIG. 23).

Example XX Preparation of Multilayer Capsules Templated on Oleic Acid Cores and Stabilized by Octadecyl Derivative of Anionically Modified Chitosan Oligocaccharide Capsules templated on oleic acid was prepared according to procedure described in Example XIX. The resulted capsules were characterized to be 170 nm in diameter and have zeta potential equal to −17 mV. Capsules were covered by multilayer shells according to procedure describing in Example XVIII. The resulted 8-layer-capsules were characterized to be 260 nm in diameter and have zeta potential equal to −29 mV. Gradual increase in average diameters of capsules as well as typical zigzag shape of the zeta potential plot conforms alternating adsorption of the polyelectrolytes and strong electrostatic stabilization of the capsules (FIG. 24, FIG. 25). Moreover, obtained results confirmed that anionic layers are more preferred and provide better stabilization of capsules.

Example XXI Determination of the Effect of Degree of Hydrophobic Modification and Concentration of Polysaccharide on the Parameters Describing Nanocapsules Templated on Oleic Acid Cores Stabilized by Hy-C18x Hyaluronate modified with octadecyl side chains (4.5% of substitution) was dissolved in 0.1M NaCl (1 g/L or 5 g/L) and mixed vigorously for 60 minutes using magnetic stirrer (500 rpm) in order to provide complete dissolution of polysaccharide. Such aqueous solutions were then mixed with oleic acid (100:1 v/v), vortexed for 5 minutes and emulsified for 30 minutes at room temperature in ultrasonic bath (540 W, 1-second pulse, 2-second break). Size of the resulted capsules was determined using DLS to be ca. 780 nm and ca. 710 nm for capsules stabilized by Hy-C18x of c=1 g/L or 5 g/L, respectively, while zeta potentials were equal to −19 mV or −16 mV, respectively. The obtained results compared to those presented in Example IV indicate that for long hydrophobic chains it is preferred to synthesize materials of low degree of substitution of side chains. Moreover, poor stability of obtained capsules regardless the concentration of polysaccharide was also showed (FIG. 26).

Table 2 Parameters of capsules stabilized by Hy-C6 and Hy-C8, respectively, templated on oleic acid cores at different times after preparation (DLS measurements)

TABLE 2

Parameters of capsules stabilized by Hy-C6 and Hy-C8, respectively, templated on oleic acid cores at different times after preparation (DLS measurements).

| Days after sonication | Hy-C6 | | | Hy-C8 | | |
| --- | --- | --- | --- | --- | --- | --- |
| | Zeta potential (mV) | Diameter (nm) | PDI | Zeta potential (mV) | Diameter (nm) | PDI |
| 0 | −20.7 | 501.9 | 0.40 | −26.7 | 707.8 | 0.25 |
| 2 | −22.1 | 363.9 | 0.29 | −19.8 | 294.0 | 0.42 |
| 5 | −21.1 | 378.4 | 0.23 | −21.8 | 379.3 | 0.20 |
| 8 | −20.9 | 259.7 | 0.21 | −22.0 | 245.4 | 0.24 |
| 9 | −20.4 | 230.1 | 0.22 | −21.0 | 264.6 | 0.23 |
| 12 | −20.1 | 264.6 | 0.21 | −22.2 | 252.1 | 0.23 |
| 14 | −19.2 | 310.7 | 0.17 | −21.1 | 226.8 | 0.24 |

Table 3 Parameters of capsules stabilized by Hy-C12 and Hy-C18, respectively, templated on oleic acid cores at different times after preparation (DLS measurements).

TABLE 3

Parameters of capsules stabilized by Hy-C12 and Hy-C18, respectively, templated on oleic acid cores at different times after preparation (DLS measurements).

| Days after sonication | Hy-C12 | | | Hy-C18 | | |
| --- | --- | --- | --- | --- | --- | --- |
| | Zeta potential (mV) | Diameter (nm) | PDI | Zeta potential (mV) | Diameter (nm) | PDI |
| 0 | −22.10 | 207.1 | 0.51 | −20.9 | 326.6 | 0.50 |
| 3 | −19.87 | 105.2 | 0.59 | −20.2 | 254.3 | 0.43 |
| 5 | −20.20 | 136.2 | 0.61 | −20.6 | 215.1 | 0.47 |
| 9 | −19.67 | 113.1 | 0.54 | −20.3 | 160.0 | 0.47 |
| 12 | −18.57 | 132.3 | 0.51 | −18.5 | 184.8 | 0.49 |
| 14 | −19.90 | 110.3 | 0.46 | — | — | — |

Table 4 Parameters of capsules stabilized by Hy-C12 and Hy-C18, respectively, templated on oleic acid cores before and after acidification of the suspension (DLS measurements).

TABLE 4

Parameters of capsules stabilized by Hy-C12 and Hy-C18, respectively, templated on oleic acid cores before and after acidification of the suspension (DLS measurements).

| | Hy-C12 | | | Hy-C18 | | |
|---|---|---|---|---|---|---|
| | Zeta potential (mV) | Diameter (nm) | PDI | Zeta potential (mV) | Diameter (nm) | PDI |
| pH 7 | −21.7 | 281.7 | 0.37 | −20.8 | 124.3 | 0.37 |
| pH 1.4 | −1.1 | 313.9 | 0.25 | −1.2 | 132.5 | 0.29 |

Table 5 Parameters of capsules stabilized by Hy-C12 and Hy-C18, respectively, templated on either linseed oil or argan oil (DLS measurements).

TABLE 5

Parameters of capsules stabilized by Hy-C12 and Hy-C18, respectively, templated on either linseed oil or argan oil (DLS measurements).

| | Hy-C12 | | | Hy-C18 | | |
|---|---|---|---|---|---|---|
| | Zeta potential (mV) | Diameter (nm) | PDI | Zeta potential (mV) | Diameter (nm) | PDI |
| Linseed oil | −19.0 | 184.8 | 0.81 | −19.9 | 535.6 | 0.76 |
| Arian oil | −20.8 | 711.4 | 0.52 | — | — | — |

Table 6 Parameters of capsules templated on oleic acid cores stabilized by dodecyl derivative of cationally modified chitosan (CChit-C12) at different times after preparation thereof (DLS measurements)

TABLE 6

Parameters of capsules templated on oleic acid cores stabilized by dodecyl derivative of cationically modified chitosan (CChit-C12) at different times after preparation thereof (DLS measurements).

| | CChit-C12 | | |
|---|---|---|---|
| Days after sonication | Zeta potential (mV) | Diameter (nm) | PDI |
| 0 | 23.7 | 326.1 | 0.18 |
| 2 | 23.1 | 337.6 | 0.31 |
| 7 | 25.3 | 310.5 | 0.23 |
| 9 | 25.0 | 275.4 | 0.33 |
| 11 | 23.2 | 271.1 | 0.22 |
| 14 | 24.6 | 258.1 | 0.21 |

What is claimed is:

1. A nanocapsule of diameter below 1 μm, used for delivery of lipophilic compounds, said nanocapsule comprises:
   a) a liquid core for delivery of lipophilic compounds, wherein the core material is selected from among oleic acid, isopropyl palmitate, fatty acids, oils, extracts of natural origin, and mixtures thereof, wherein said oils are selected from linseed oil, soybean oil, argan oil and mixtures thereof;
   b) a shell made from charged hydrophobically modified polysaccharides, wherein the hydrophobically modified polysaccharides are selected from: Hy-Cx, CChit-C12 or oCh-C18-sulf, where:

Hy-Cx, wherein x=6 or 8 or 12 or 18, and Hy-Cx is a hyaluronate derivative of the following structure:

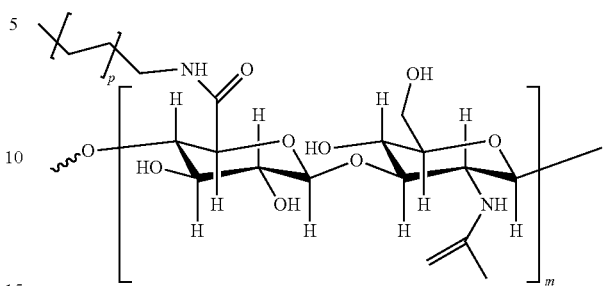

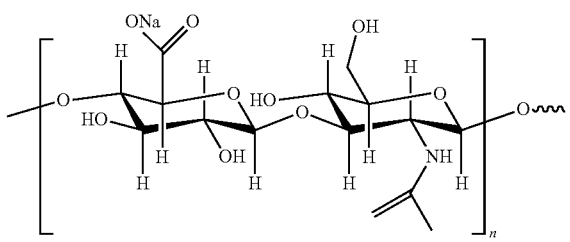

where p is an integer selected from: 2, 3, 5 or 8, m is an integer equal to about 10 for HyC6 and HyC8, about 22 for HyC12 and HyC18x and about 7 for HyC18, while n is an integer equal to about 472 for HyC6 and HyC8, about 460 for HyC12 and HyC18x and about 475 for HyC18, CChit-C12 is dodecyl derivative of cationically modified chitosan of the following formula:

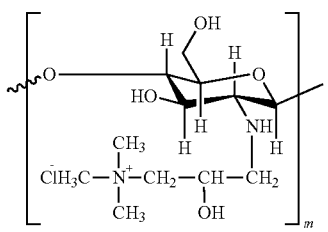

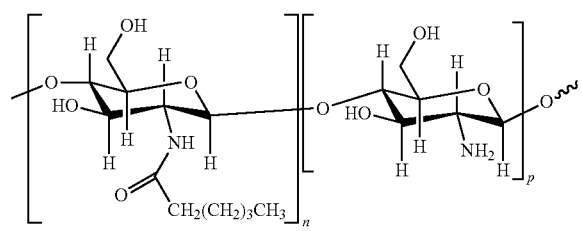

where m is an integer equal to about 200, n is an integer equal to about 6, and p is an integer equal to about 88, and oCh-C18-sulf is an octadecyl derivative of anionically modified chitosan oligosaccharide of the following structure:

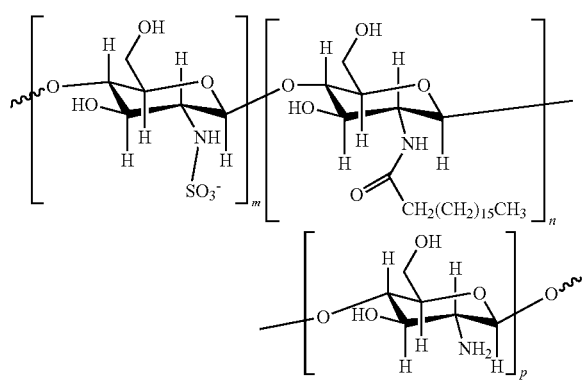

where m is an integer equal to about 9, n is an integer equal to about 1, and p is an integer equal to about 5; and wherein the nanocapsules are stabilized by the charged hydrophobically modified polysaccharides due to their amphiphilic character.

2. The nanocapsule of claim 1 wherein the degree of substitution of hydrophobic chains in said modified polysaccharide varies between 0.1-40%.

3. The nanocapsule of claim 1 wherein the shell of said capsule is covered by a polyelectrolyte film consisting of biocompatible polyelectrolyte or its derivative of natural origin and is selected from the group consisting of chitosan, dextran, starch, hydroxypropyl cellulose, and glycosaminoglycans and synthetic polyelectrolytes selected from among poly-L-lysine, polyornityne, poly (D-glutamic acid), derivatives of poly(lactic acid), polystyrenesulfonate, poly (diallildimethylammonium chloride), polyallylamine hydrochloride, and polyethyleneimine.

4. The nanocapsule of claim 1 wherein fluorescent dye, vitamin or active pharmaceutical ingredient can be delivered while encapsulated within the oil core.

5. An aqueous suspension containing the nanocapsules of claim 1.

6. The nanocapsule of claim 1, wherein the integers m, n and p of the dodecyl derivative of cationically modified chitosan is calculated for chitosan of a molar mass equal to 100,000 g/mol.

7. The nanocapsule of claim 3, wherein said glycosaminoglycans are selected from the group consisting of hyaluronic acid, heparan sulfate, heparin sulfate, keratan sulfate, chondroitin sulfate, and dermatan sulfate.

8. The nanocapsule of claim 1, wherein the hydrophobically modified polysaccharides have a pH of between 2-12.

9. The nanocapsule of claim 1, wherein the hydrophobically modified polysaccharides are ionic.

10. The nanocapsule of claim 9, wherein the hydrophobically modified ionic polysaccharides possess stable electrostatic charge provided by ionic groups within polymeric chains, wherein the ionic groups are selected from the group consisting of carboxylic, sulfonic, sulfate, phosphate, ammonium, pyridine, and phosphono groups.

* * * * *